(12) United States Patent
Li et al.

(10) Patent No.: US 11,967,063 B2
(45) Date of Patent: Apr. 23, 2024

(54) AUTOMATIC BIO-SPECIMEN INSPECTION SYSTEM AND INSPECTION METHOD THEREOF

(71) Applicant: INDUSTRIAL TECHNOLOGY RESEARCH INSTITUTE, Hsinchu (TW)

(72) Inventors: Shang-Kun Li, Taichung (TW); Shu Huang, Zhudong Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 379 days.

(21) Appl. No.: 17/182,740

(22) Filed: Feb. 23, 2021

(65) Prior Publication Data

US 2021/0304404 A1    Sep. 30, 2021

Related U.S. Application Data

(60) Provisional application No. 63/001,588, filed on Mar. 30, 2020.

(30) Foreign Application Priority Data

Dec. 18, 2020 (TW) .................. 109144987

(51) Int. Cl.
*G06T 7/00* (2017.01)
*A61B 10/00* (2006.01)
(Continued)

(52) U.S. Cl.
CPC ........ *G06T 7/0012* (2013.01); *A61B 10/0045* (2013.01); *G06N 3/0475* (2023.01);
(Continued)

(58) Field of Classification Search
None
See application file for complete search history.

(56) References Cited

U.S. PATENT DOCUMENTS 7,261,103 B2    8/2007   Katz
8,734,423 B2    5/2014   Morelock et al.
(Continued)

FOREIGN PATENT DOCUMENTS

CN        2850513 Y    12/2006
CN      201167979 Y    12/2008
(Continued)

OTHER PUBLICATIONS

Q. Wang, China Develops Intelligent Robots for Throat Swab Sampling of Coronavirus Tests. Global Times. Beijing, China, Mar. 2020, [online] Available: https://www.globaltimes.cn/content/1182175.shtml. (Year: 2020).*

(Continued)

*Primary Examiner* — Sean M Conner
(74) *Attorney, Agent, or Firm* — Birch, Stewart, Kolasch & Birch, LLP

(57) ABSTRACT

An automatic bio-specimen inspection system includes an inspection device, an image processing module, a spatial learning module, a path generation module and a motion device. The inspection device is used to approach an inspection site for performing a bio-specimens collection and/or inspection. The image processing module is used to capture and process a plurality of 2D images of the inspection site. The spatial learning module is used to generate a 3D spatial information of the inspection site according to the 2D images. The path generation module is used to generate an inspection path information based on the 3D spatial information. The motion device is used to move the inspection (Continued)

device to the inspection site according to the inspection path information for performing the inspection operation.

15 Claims, 4 Drawing Sheets

(51) Int. Cl.
*G06N 3/0475* (2023.01)
*G06N 3/094* (2023.01)

(52) U.S. Cl.
CPC ...... *G06N 3/094* (2023.01); *A61B 2562/0247* (2013.01); *G06T 2207/10024* (2013.01); *G06T 2207/10028* (2013.01); *G06T 2207/20081* (2013.01); *G06T 2207/20084* (2013.01); *G06T 2207/30004* (2013.01)

(56) References Cited

U.S. PATENT DOCUMENTS

| | | | |
|---|---|---|---|
| 9,808,182 | B2 | 11/2017 | Johnson et al. |
| 10,390,734 | B2 | 8/2019 | Johnson et al. |
| 2019/0042859 | A1* | 2/2019 | Schubert ............... B62D 1/28 |
| 2020/0030979 | A1 | 1/2020 | Bank et al. |
| 2021/0181754 | A1* | 6/2021 | Cui ............... B60W 60/0011 |
| 2022/0379472 | A1* | 12/2022 | Takebayashi .......... B25J 9/1664 |

FOREIGN PATENT DOCUMENTS

| | | |
|---|---|---|
| CN | 105395295 A | 3/2016 |
| CN | 205126477 U | 4/2016 |
| CN | 106235998 A | 12/2016 |
| CN | 107802364 A | 3/2018 |
| CN | 109045452 A | 12/2018 |
| CN | 105911992 B | 2/2019 |
| CN | 109996492 A | 7/2019 |
| CN | 209808418 U | 12/2019 |
| CN | 110755025 A | 2/2020 |
| CN | 110782395 A | 2/2020 |
| TW | 201918348 A | 5/2019 |
| WO | WO 2017/084301 A1 | 4/2017 |

OTHER PUBLICATIONS

Sitzmann, Vincent, et al. "Deepvoxels: Learning persistent 3d feature embeddings." Proceedings of the IEEE/CVF Conference on Computer Vision and Pattern Recognition. 2019. (Year: 2019).*
Mohammadi, Mehdi, Ala Al-Fuqaha, and Jun-Seok Oh. "Path planning in support of smart mobility applications using generative adversarial networks." 2018 IEEE International Conference on Internet of Things (iThings) and IEEE Green Computing and Communications (GreenCom). IEEE, 2018. (Year: 2018).*
Taiwanese Office Action and Search Report for Taiwanese Application No. 109144987, dated Jul. 15, 2021.
He et al., "Endoscopic Path Planning in Robot-Assisted Endoscopic Nasal Surgery", IEEE Access, 2020, vol. 8, pp. 17039-17048.
Koga et al., "Development of Oral Rehabilitation Robot for Massage Therapy", 6th International Special Topic Conference on ITAB, 2007, Tokyo, pp. 111-114.
Li et al., "Clinical Application of Intelligent Oropharyngeal-swab Robot: Implication for COVID-19 Pandemic", European Respiratory Journal, 2020, total 10 pages.
Li et al., "Spatial Motion Constraints Using Virtual Fixtures Generated by Anatomy", IEEE Transactions on Robotics, Feb. 2007, vol. 23, No. 1, pp. 4-19.
Wang et al., "Design of a Low-cost Miniature Robot to Assist the COVID-19 Nasopharyngeal Swab Sampling", arXiv, 2005, total 5 pages.
Zheng et al., "Safety Tracking Motion Control Based on Forbidden Virtual Fixtures in Robot Assisted Nasal Surgery", IEEE Access, 2018, vol. 6, pp. 44905-44916.

* cited by examiner

AUTOMATIC BIO-SPECIMEN INSPECTION SYSTEM AND INSPECTION METHOD THEREOF

This application claims the benefit of U.S. provisional patent application Ser. No. 63/001,588, filed on Mar. 30, 2020, and Taiwan patent application Serial No. 109144987, filed on Dec. 18, 2020, the subject matters of which are incorporated herein by references.

BACKGROUND OF THE DISCLOSURE

Field of the Disclosure

The disclosure relates in general to a bio-specimen inspection system and the inspection method thereof as well as the applications of the same, and more particularly to an automatic bio-specimen inspection system and the inspection method thereof as well as the applications of the same.

Description of the Related Art

With the spread of the new type of coronary pneumonia (such as, COVID-19) and other respiratory diseases, in order to find a confirmed infected person, medical staff need to conduct a test on the suspected infected person first. If the case is confirmed, the infection can be notified, and the infected person can be treated and tracked. Typically, the bio-specimens of the suspected infected person are collected and inspected by hands of the medical personnel wearing protective clothing all over the body.

However, because the traditional bio-specimens collection and/or inspection require a face-to-face operation of the medical staff and the subjects, the infection risk of the medical staff can be increased during the operation. Fortunately, safety inspection kiosks or transparent acrylic baffles have been used to isolate medical staff from the subjects to reduce the infection risk of medical staff. But, the bio-specimens collection and/or inspection still consume medical staff a lot of manpower and time, and may make the medical staff overloaded when a large number of suspected cases occur. Therefore, how to automate the bio-specimens collection and/or inspection avoiding of medical manpower consumption has become an important issue in this technical field.

To automate the bio-specimens collection and/or inspection, it is necessary to acquire the three-dimensional (3D) spatial information of the inspection site for performing the bio-specimens collection and/or inspection, since the inspection site is usually located in the body cavity of the subjects. Although a plurality of prior technologies, such as a computerized tomography (CT) scan, a magnetic resonance imaging (MRI) scan or an X-ray imaging technology, have been applied to acquire the 3D spatial information of the inspection site, these technologies are not only expensive, large in size and complicated in operation, but also may make the subjects risking to radiation exposure.

The current 3D optical photography technology is quite mature, it can be used to directly capture the 3D images of the inspection site. However, the size of the 3D optical photography camera is relatively large not suitable for being inserted into the body cavity of the subjects, thus it may hinder the bio-specimens collection and/or inspection.

In sum, to make the hospital human resources more effective, the pertinent industry is seeking for solutions of automating the bio-specimens collection and/or inspection. However, the traditional solutions at least have the following three difficulties: (1) using two-dimensional (2D) image technology to acquire the 3D spatial information of the inspection site not only lacks of depth information, but also affects the accuracy and safety of the automatic bio-specimens inspection system, (2) due to the narrow body cavity (e.g. an oral) size, it is difficult to use a commercially 3D optical photography camera to create 3D images of the body cavity (e.g. the oral images), (3) the prior art solutions may be too specific to certain bio-specimens inspection sites to be available for various bio-specimens inspection sites.

Therefore, there is a need to provide an automatic bio-specimen inspection system and the inspection method thereof as well as the applications of the same to overcome the drawbacks of the prior art.

SUMMARY OF THE DISCLOSURE

One aspect of the present disclosure is to provide an automatic bio-specimen inspection system, wherein the automatic bio-specimen inspection system includes an inspection device, an image processing module, a spatial learning module, a path generation module and a motion device. The inspection device is used to approach an inspection site for performing a bio-specimens collection and/or inspection. The image processing module is used to capture and process a plurality of 2D images of the inspection site. The spatial learning module is used to generate a 3D spatial information of the inspection site according to the 2D images. The path generation module is used to generate an inspection path information based on the 3D spatial information. The motion device is used to move the inspection device to the inspection site according to the inspection path information for performing the bio-specimens collection and/or inspection.

Another aspect of the present disclosure provides an automatic bio-specimen inspection method, wherein the method includes steps as follows: an inspection device is used to approach an inspection site of bio-specimens. A plurality of 2D images of the inspection site is captured and processed by an image processing module. A 3D spatial information of the inspection site are generated by a learning module according to the 2D images. An inspection path information is generated by a path generation module based on the 3D spatial information. The inspection device is moved to the inspection site according to the inspection path information by a motion device for performing an bio-specimens collection and/or inspection.

Yet another aspect of the present disclosure provides a non-volatile computer-readable recording medium, wherein the non-volatile computer-readable recording medium stores a program code, and the program code can be executed by a processor to execute the above-mentioned automatic bio-specimen inspection method.

Further another aspect of the present disclosure provides a non-volatile computer-readable recording medium, wherein the non-volatile computer-readable recording medium stores a set of program codes, and the set of program codes can be executed by a processor to control an automatic bio-specimen inspection system performing the following steps of: commanding an inspection device to approach an inspection site of bio-specimens; commanding an image processing module to capture and process a plurality of 2D images of the inspection site; commanding a spatial learning module to generate a 3D spatial information of the inspection site according to the 2D images; commanding a path generation module to generate an inspection path information based on the 3D spatial information and commanding a motion device to move the inspection device to the inspection site according to the inspection path information for performing an inspection operation.

BRIEF DESCRIPTION OF THE DRAWINGS

The above and other aspects of the disclosure will become better understood with regard to the following detailed description of the preferred but non-limiting embodiment(s). The following description is made with reference to the accompanying drawings.

DETAILED DESCRIPTION OF THE DISCLOSURE

The present disclosure provides an automatic bio-specimen inspection system and the inspection method thereof as well as the applications of the same, which can achieve the automation of bio-specimens collection and/or inspection, so as to save the cost of medical manpower. The above and other aspects of the disclosure will become better understood by the following detailed description of the preferred but non-limiting embodiment(s). The following description is made with reference to the accompanying drawings:

Several embodiments of the present disclosure are disclosed below with reference to accompanying drawings. However, the structure and contents disclosed in the embodiments are for exemplary and explanatory purposes only, and the scope of protection of the present disclosure is not limited to the embodiments. It should be noted that the present disclosure does not illustrate all possible embodiments, and anyone skilled in the technology field of the disclosure will be able to make suitable modifications or changes based on the specification disclosed below to meet actual needs without breaching the spirit of the disclosure. The present disclosure is applicable to other implementations not disclosed in the specification.

Figure 1:
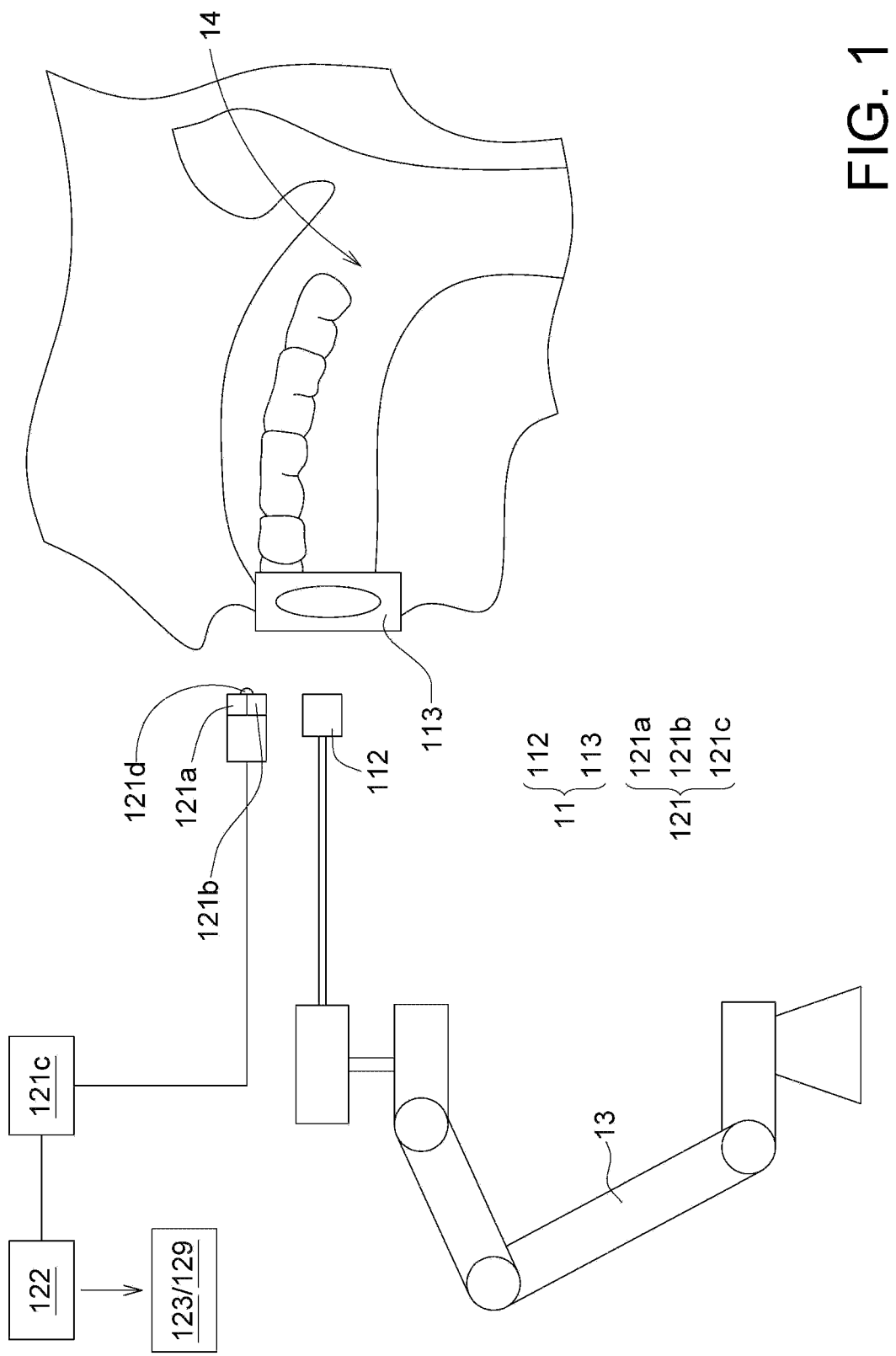
FIG. 1 is a block diagram of an automatic bio-specimen inspection system according to one embodiment of the present disclosure.

FIG. 1 is a block diagram of an automatic bio-specimen inspection system 10 according to one embodiment of the present disclosure, wherein the automatic bio-specimen inspection system 10 includes an inspection device 11, an image processing module 121, a spatial learning module 122, a path generation module 123 and a motion device 13.

The inspection device 11 is used to approach an inspection site 14 for performing bio-specimens collection and/or inspection. For example, in some embodiments of the present disclosure, the inspection device 11 may include a swab 112 (or other tools with the same function, such as a sampling rods, a sample collector, etc.) used to be inserted into the oral, nose, and/or throat cavity of the organism for collecting and/or inspecting. In order to facilitate the swab 112 (a sampling rods, a sample collector, etc.) to pass through the subject's oral, nose and/or throat cavity, the inspection device 11 may additionally include an articulator 113 which is used to expand the space between subject's mandible and maxilla to enlarge the oral space and provide a stable channel for the swab 112, the sampling rod, and the sample collector to enter the oral, nose and/or throat cavity.

However, the inspection device 11 is not limited to this regard. Any device, component, element, instrument or consumable that can be used for performing specimen collection or inspection in the oral, nose and/or throat cavity or in other chambers, lumens, channels, or tissue locations either in the body or on any position outside the body of humans or living organisms does not exceed the spirit of the inspection device 11.

The motion device 13 is electrically connected to the image processing module 121, the spatial learning module 122, and the path generation module 123, wherein the motion device 13 is used to move the inspection device 11 to the inspection site 14 in respond to the commands (e.g. an inspection path information) receiving from the path generation module 123. In one embodiment of the present disclosure, the motion device 13 may be a robot arm. The swab 112 of the inspection device 11 can be directly arranged at the end of the robot arm, and the swab 112 is inserted into the oral, nose and/or throat cavity of the subject by the robot arm.

Figure 2:
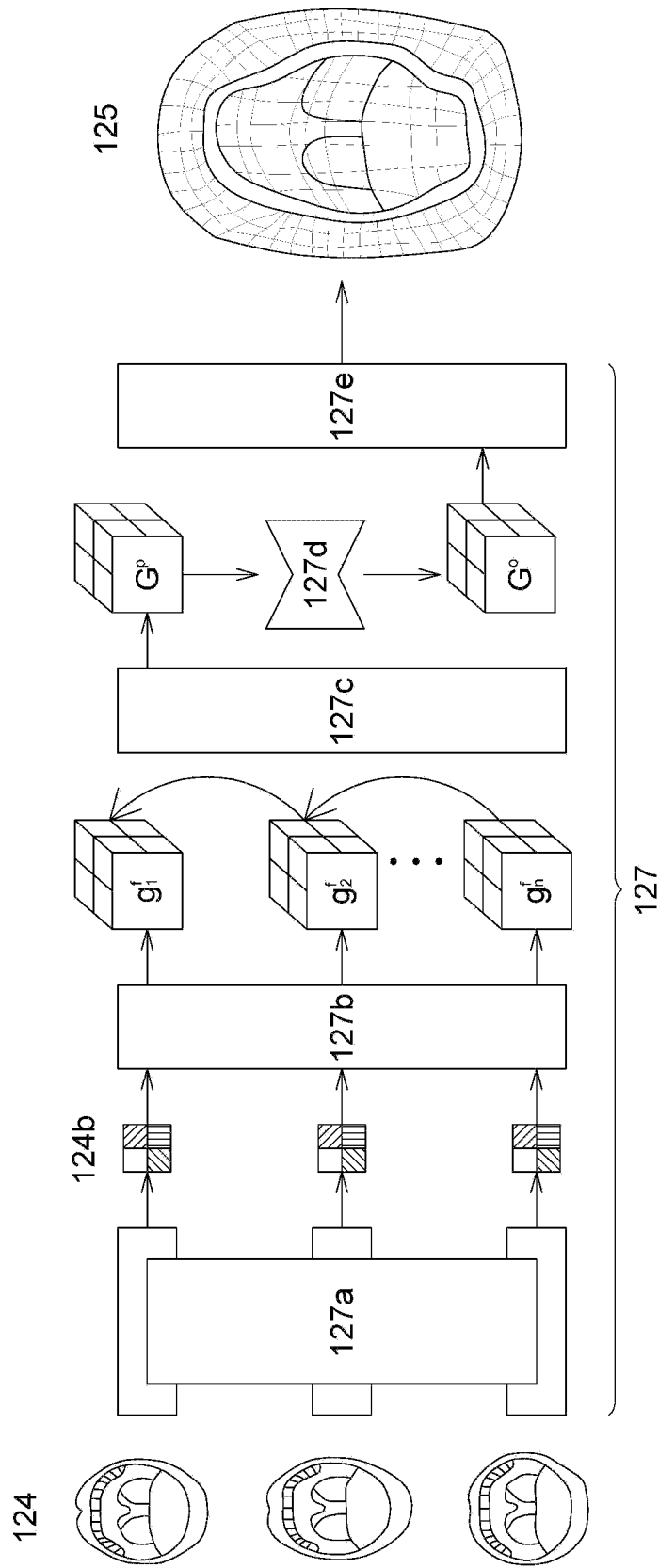
FIG. 2 is a schematic diagram illustrating the process of using a 3D learning network to convert a plurality of 2D images into a 3D information according to one embodiment of the present disclosure.
Figure 3:
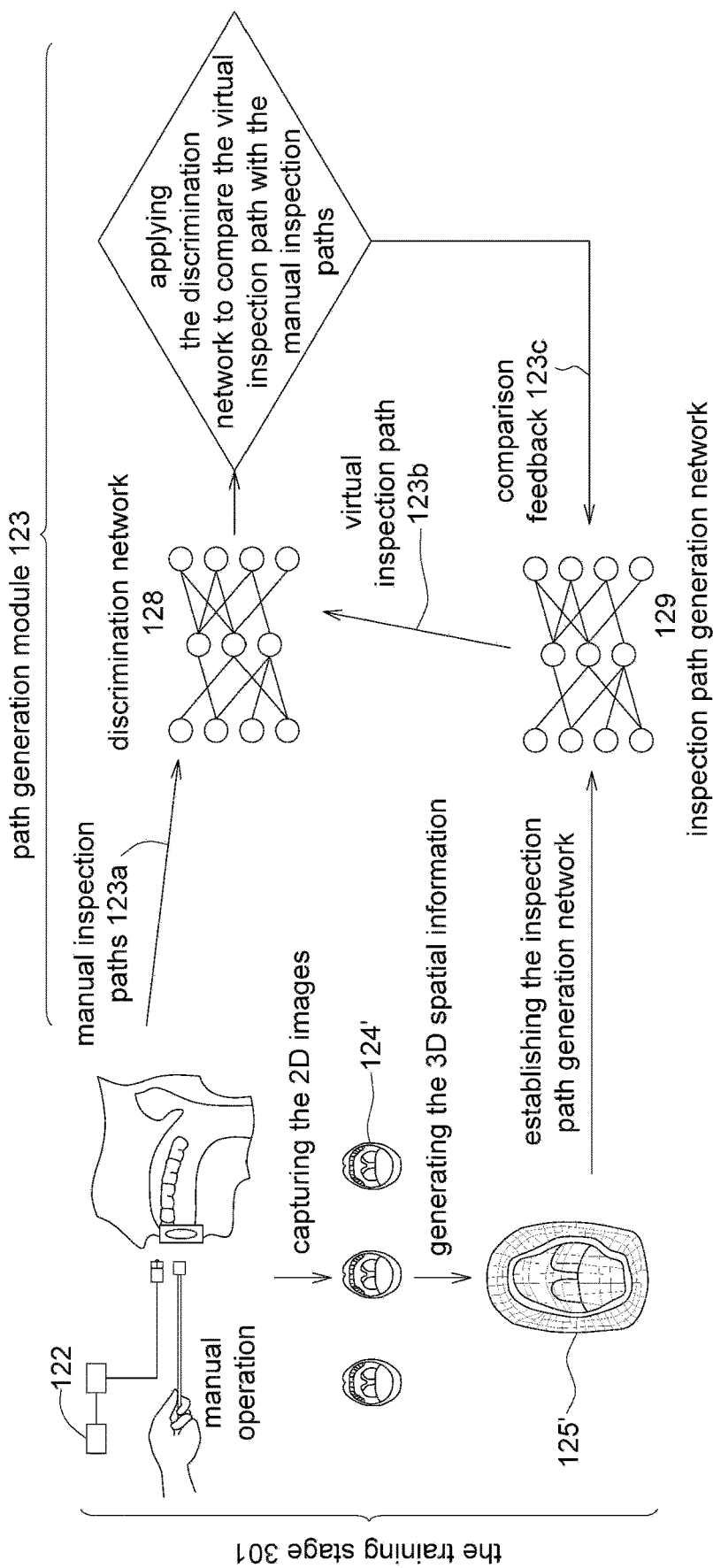
FIG. 3 is a schematic diagram illustrating a flowchart of generating a virtual inspection path using an inspection path generation network of a path generation module according to one embodiment of the present disclosure.

Please refer to FIGS. 1, 2 and 3 at the same time. The image processing module 121 is used to capture and process a plurality of 2D images 124 of the inspection site 14. The spatial learning module 122 is used to generate a 3D spatial information 125 of the inspection site 14 according to the captured 2D images 124. The path generation module 123 is used to generate an inspection path information 126 based on the 3D spatial information 125.

In some embodiments of the present disclosure, the image processing module 121 includes a light source 121a, an image capturing unit 121b, and an image processing unit 121c. The light source 121a may include (but is not limited to) a light-emitting diode (LED) element, which may be used to provide light illumination to the inspection site 14. The image capturing unit 121b may be a light detecting unit, which includes (but is not limited to) at least one photo-electric transducering element, such as a photodiode, a charge-coupled device (CCD) or an Intensified CCD (ICCD), and can be used to capture optical information such as brightness, gray scale, and color (RGB) of the inspection site 14. The image processing unit 121c is used to convert the optical information into the 2D images 124. However, the image processing unit 121c is not limited to this regard, and any software, hardware, firmware, or any combination thereof used for processing images does not exceed the spirit of the image processing unit 121c.

In the present embodiment, the image capturing unit 121b can be disposed adjacent to one side of the swab 112, fixed to the inspection device 11, and can be moved in three dimensions with the swab 112 in the oral, nose, and/or throat cavity. In one embodiment, the image processing module 121 may further include a camera driver (not shown) for driving a camera of the image capturing unit 121b to capture a plurality of the 2D images 124 from different viewing angles.

FIG. 2 is a schematic diagram illustrating the process of using a 3D learning network 127 to convert a plurality of the 2D images 124 into the 3D spatial information 125 according to one embodiment of the present disclosure. In the present embodiment, the 3D learning network 127 is included in the spatial learning module 122 used to generate the 3D spatial information 125 of the inspection site 14 based on the plurality of the 2D images 124.

In detail, a plurality of 2D projection grid features 124b are firstly generated by inputting the plurality of the 2D images 124 into an image encoder 127a. After that, a feature matching process is performed using an unprojection module 127b to project the features of these 2D projection grid features 124b onto a 3D grid respectively to form a plurality of 3D grid features $\overline{G_n^f}$ (n=1–f).

Next, a recurrent neural network 127c is used to compare the features of different 3D grid features, and fuse these 3D grid features $\overline{G_n^f}$ (n=1–f) to form the 3D grid feature map $G^p$. A 3D grid reasoning module 127d is then applied to calculate the matching cost product (matching cost volume) using 3D convolutional neural networks; and the matching cost product of the 3D grid feature map $G^p$ is decoded to form a 3D grid feature map $G^o$ with 3D volume/surface/disparity information.

After that, according to the 3D spatial information of the 3D grid feature map $G^o$, a 3D image of the inspection site 14 can be simulated in the form of 3D voxel occupancy grids by a projection module 127e, wherein the 3D image includes the 3D spatial information 125. In the present embodiment, the 3D spatial information 125 further includes a plurality of depth information, and a plurality of color information expressed in the form of RGBD.

Figure 4:
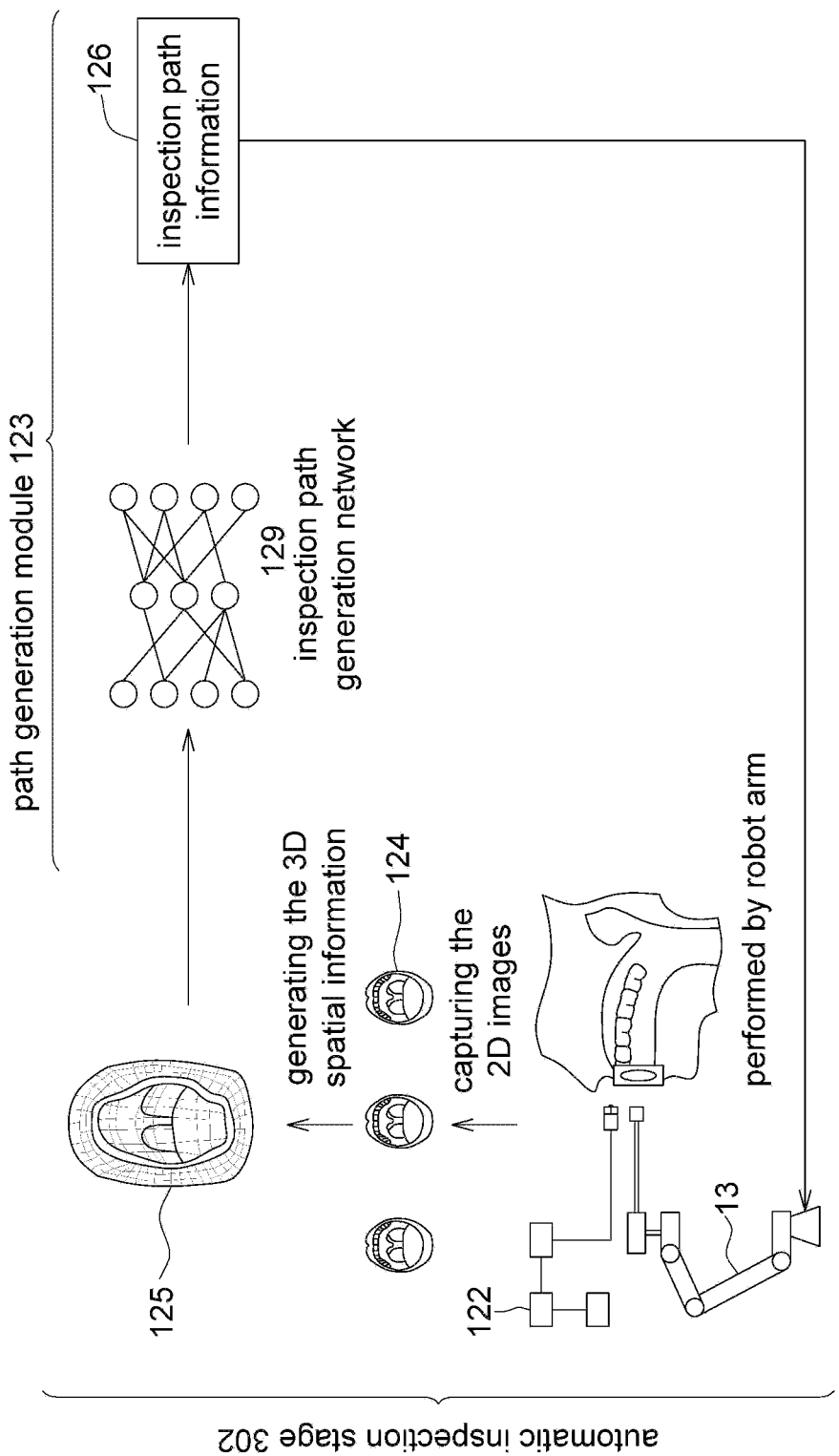
FIG. 4 is a schematic diagram illustrating a flowchart of generating automatic inspection paths using a 3D learning network and an inspection path generation network according to one embodiment of the disclosure.

Following the above, as shown in FIG. 4, the inspection path information 126 can be generated by the path generation module 123 based on the 3D spatial information 125 obtained from the process as depicted in FIG. 2.

As shown in FIGS. 1, 3 and 4, in the present embodiment, the path generation module 123 includes an inspection path generation network 129, which can generate the inspection path information 126 and provide it to the motion device 13; and the motion device 13 can move the swab 112 of the inspection device 11 to the inspection site 14 in the oral, nose and/or throat cavity according to the inspection path information 126.

FIG. 3 is a schematic diagram illustrating a flowchart of generating a virtual inspection path using the inspection path generation network 129 of the path generation module 123 according to one embodiment of the present disclosure. The process of generating the virtual inspection paths can be referred to as a "training phase 301".

In the training phase 301, firstly a plurality of manual operations for carrying bio-specimens collection and/or inspection are performed on a single or multiple organisms to obtain several sets of 2D images 124'; a plurality of 3D spatial information 125' are then generated by using the spatial learning module 122; a plurality of manual inspection paths 123a of the inspection device 11 and the 3D spatial information 125' corresponding to each of the manual inspection paths 123a during the manual operations are recorded. The inspection path generation network 129 can be constructed based on the plurality of the manual inspection paths 123a and the plurality of the 3D spatial information 125' by using neural network technologies. In detail, each manual operation can obtain a set of 2D images 124', and each set of 2D images 124' can correspond to a 3D spatial information 125'. That is, each of the manual inspection paths 123a corresponds to a 3D spatial information 125'.

In the present embodiment, for example, the manual operations can be performed by qualified medical staff or inspectors using the swab 112 (including the LED light source 121a and the image capturing unit 121b) of the inspection device 11 for collecting and/or inspecting bio-specimens in the oral, nose, and/or throat cavities of the same or different subject; and the manual inspection paths 123a and the 2D images 124' of the swabs 112 of the inspection device 11 captured during the manual operations are collected and records the image processing module 121.

Subsequently, various 3D spatial information 125' can be then generated by the spatial module 122 according to the 2D images 124' of the oral, nose, and throat cavity captured and recorded by the image processing module 121; and the inspection path generation network 129 an be established to generate the virtual inspection path 123b.

In some embodiments of the present disclosure, the automatic bio-specimen inspection system 10 may further include a pressure sensor 121d, arranged on the swab 112 of the inspection device 11, and used to sense the contact stress between the swab 112 of the inspection 11 and the inspection site 14, in order to confirm whether the swab 112 is actually contact to the inspection site 14, or to measure the magnitude of the contact stress. Meanwhile, the contact stress can be fed back to the path generation module 123.

Next, as shown in FIG. 3, a discrimination network 128 is applied to compare the virtual inspection path 123b with the manual inspection paths 123a and then providing a comparison feedback 123c to the inspection path generation network 129. Such that, the subsequent generated virtual inspection path 123b can be closer to the manual inspection paths 123a, and the inspection path generation network 129 can be further adjusted or optimized in the training stage, and for use in the automatic inspection stage.

FIG. 4 is a schematic diagram illustrating a flowchart of generating automatic inspection paths using a 3D learning network and the inspection path generation network 129 according to one embodiment of the disclosure. The process of generating automatic inspection paths can be referred to as the "automatic inspection stage 302".

In the automatic inspection stage 302, the image processing module 121 is used to capture a plurality of 2D images 124 of the oral, nose, and/or throat cavity of the current subjects; and 3D spatial information 125 of the inspection site 14 can be generated by the spatial learning module 122 based on the captured 2D images 124. Next, inspection path information 126 can be generated by the inspection path generation network 129 of the path generation module 123 based on the 3D spatial information 125. Wherein the inspection path information 126 includes at least one inspection path. The inspection path information 126 generated by the path generation module 123 is then provided to the motion device 13. It should be noted that, the inspection path generation network 129 applied in the automatic inspection stage 302 can be a path generation network created and then being adjusted/optimized in the training stage 301.

Subsequently, the motion device 13 moves the swab 112 of the inspection device 11 to the inspection site 14 according to the inspection path to perform the automatic bio-specimens collection and/or inspection. In one embodiment of the present disclosure, the motion device 13 may be a robot arm used to perform the automatic bio-specimens collection and/or inspection in the automatic inspection stage 302.

The software, application programs, data or computational logic used by the automatic bio-specimen inspection system 10 mentioned above can be integrated to form a non-volatile computer-readable recording medium stored in a non-volatile memory storage device (e.g., a magnetic storage, compact disk, flash memory or other suitable integrated circuit) or computer network. Moreover, this non-volatile computer-readable recording medium has a set of program codes, and the automatic bio-specimen inspection system 10 can be controlled by a processor (for example, the central processing unit (CPU) of a computer) to execute the following steps of: commanding the image processing module 121 to capture and process a plurality of 2D images 124 of the inspection site 14; commanding the spatial learning module 122 to generate a 3D spatial information 125 of the inspection site 14 according to the 2D images 124; commanding the path generation module 123 to generate an inspection path information 126 based on the 3D spatial information 125 and commanding the motion device 13 to move the swab 112 of the inspection device 11 to the inspection site 14 according to the inspection path information 126 for performing bio-specimens collection and/or inspection. Of noted that the above-mentioned bio-specimens collection and/or inspection implemented by the automatic bio-specimen inspection system 10 does not require any manual operation.

According to the above description, the embodiments of the disclosure provide an automatic bio-specimen inspection system and the inspection method thereof as well as the applications of the same. The automatic bio-specimen inspection system includes an inspection device, an image processing module, a spatial learning module, a path generation module and a motion device. The inspection device is used to approach an inspection site of for performing a bio-specimen collection and/or inspection. The image processing module is used to capture and process a plurality of 2D images of the inspection site. The spatial learning module is used to generate a 3D spatial information of the inspection site according to the 2D images. The path generation module is used to generate an inspection path information based on the 3D spatial information. The motion device is used to move the inspection device to the inspection site according to the inspection path information for performing the bio-specimen collection and/or inspection. The automation of bio-specimens collection and/or inspection can be achieved without adding expensive equipment by the automatic bio-specimen inspection system, so as to save the cost of medical manpower.

The present disclosure is in response to the need for automatic bio-specimens collection and/or inspection to effectively prevent the epidemic of the new coronary pneumonia. Presently, the pertinent industry is seeking for solutions of automating the bio-specimens collection and/or inspection. But those prior art solutions that combines 2D image technology with force feedback devices to define the position of the subject's oral cavity and to provide a bio-specimens collection inspection path to a robot arm, cannot run well, due to lacking the subject's 3D spatial information. Therefore, the prior art solutions have safety concerns; and may be too specific to a certain inspection site to be available for various inspection sites. Besides, the accuracy of bio-specimens collection inspection performed by the prior art solutions may be also questionable. The present disclosure is to combine a visual image technology for rapidly reconstructing a 3D point cloud of an oral cavity with deep learning technologies for training a robot arm's picking posture, so as to make the robot arm performing a human-like operation to implement a rapid bio-specimens collection and/or inspection.

The present disclosure provides an automatic inspection system that uses a 2D image technology to form depth images (depth maps) to solve the safety problems of the traditional bio-specimens collection and/or inspection, and applies neural network learning methods to learn manual postures for bio-specimens collection and/or inspection, so that the automatic inspection system can provide a robot arm an bio-specimens collection and/or inspection path that mimics the human operation and is available for various inspection sites.

For example, in one embodiment, the present disclosure can be combined with a robot arm and a 2D camera to automatically perform bio-specimens collection and/or inspection in a body cavity, such as the oral, nose and/or throat cavity of humans or living organisms. In another embodiment, the present disclosure can create 3D images based on a plurality of 2D images and provide automatic inspection paths to the robot arm by collecting and learning manual postures for bio-specimens collection and/or inspection. In yet another embodiment, the present disclosure can use 2D images of the oral cavity as a data source for training a 3D learning network to generate a 3D depth image information of the oral, nose and/or throat cavity. For example, a plurality of 2D images of the oral, nose and/or throat cavity can be inputted into a trained 3D learning network to generate a 3D image information, and the 3D image information is used to train a robot arm inspection path generation network. The trained results are compared with a discrimination network to compare with the manual inspection paths. When the comparison result is not good, the robot arm inspection path generation network can be retrained, and these steps are repeated until these two neural networks reach a zero-sum balance. By this approach, a bio-specimens collection and/or inspection path that mimics the manual operation can be generated. Finally, the 3D learning network and the inspection path generation network can be used to generate an automatic inspection paths for the robot arm, which can replace the manual operation and can be available for various inspection sites.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An automatic bio-specimen inspection system comprising:
    an inspection device, used to approach an inspection site for performing a bio-specimens collection and/or inspection;
    an image processing module, used to capture and process a plurality of two-dimensional (2D) images of the inspection site;
    a spatial learning module, used to generate a three-dimensional (3D) spatial information of the inspection site according to the plurality of 2D images;
    a path generation module, comprising an inspection path generation network and a discrimination network used to generate an inspection path information based on the 3D spatial information; wherein the generation of the inspection path information comprises:
        performing a plurality of manual operations to capture the plurality of 2D images;
        using the spatial learning module to generate the 3D spatial information;
        recording a plurality of manual inspection paths of the inspection device and the 3D spatial information corresponding to each of the plurality of manual inspection paths;

establishing the inspection path generation network of the path generation module based on the plurality of manual inspection paths and the 3D spatial information;

using the inspection path generation network to generate a virtual inspection path based on the 3D spatial information; and applying the discrimination network to compare the virtual inspection path with the manual inspection paths and providing a comparison feedback to the inspection path generation network based on a comparison result; and a motion device, used to move the inspection device to the inspection site according to the inspection path information for performing the bio-specimens collection and/or inspection.

2. The automatic bio-specimen inspection system according to claim 1, wherein the spatial learning module comprises a 3D learning network used to generate the 3D spatial information according to the plurality of 2D images.

3. The automatic bio-specimen inspection system according to claim 1, wherein the inspection path generation network is used to generate the inspection path information based on the 3D spatial information in an automatic inspection stage.

4. The automatic bio-specimen inspection system according to claim 1, wherein the inspection site comprises an oral, nose and/or throat cavity of humans or organisms; and the inspection device further comprises an articulator and a swab.

5. The automatic bio-specimen inspection system according to claim 1, further comprising a pressure sensor arranged on the inspection device, used to sense a contact stress between the inspection device and the inspection site and to feed back the contact stress to the path generation module.

6. The automatic bio-specimen inspection system according to claim 1, wherein the image processing module comprises an image capturing unit disposed adjacent to the inspection device, used to capture the plurality of 2D images of the inspection site from different viewing angles; and the 3D spatial information comprises a plurality of depth information, and a plurality of color information expressed in a form of RGBD.

7. An automatic bio-specimen inspection method comprising:

using an inspection device to approach an inspection site for performing a bio-specimens collection and/or inspection;

using an image processing module to capture and process a plurality of 2D images of the inspection site;

using a spatial learning module to generate a 3D spatial information of the inspection site according to the plurality of 2D images;

using a path generation module to generate an inspection path information based on the 3D spatial information, wherein the generation of the inspection path information comprises:

performing a plurality of manual operations to capture the plurality of 2D images;

using the spatial learning module to generate the 3D spatial information;

recording a plurality of manual inspection paths of the inspection device and the 3D spatial information corresponding to each of the plurality of manual inspection paths;

establishing an inspection path generation network of the path generation module based on the plurality of manual inspection paths and the 3D spatial information;

using the inspection path generation network to generate a virtual inspection path based on the 3D spatial information; and applying a discrimination network to compare the virtual inspection path with the manual inspection paths and providing a comparison feedback to the inspection path generation network based on a comparison result; and using a motion device to move the inspection device to the inspection site according to the inspection path information for performing the bio-specimens collection and/or inspection.

8. The automatic bio-specimen inspection method according to claim 7, wherein the plurality of 2D images of the inspection site are captured by the image processing module from different viewing angles.

9. The automatic bio-specimen inspection method according to claim 7, wherein the generation of the 3D spatial information comprises using a 3D learning network of the spatial learning module to generate the 3D spatial information comprising a plurality of depth information, and a plurality of color information expressed in a form of RGBD.

10. The automatic bio-specimen inspection method according to claim 7, wherein the inspection path generation network of the path generation module is used to generate the inspection path information in an automatic inspection stage.

11. A non-transitory computer-readable recording medium, wherein the non-volatile computer-readable recording medium stores a program code, and the program code is executed by a processor to execute an automatic bio-specimen inspection method, comprising:

using an inspection device to approach an inspection site for performing a bio-specimens collection and/or inspection;

using an image processing module to capture and process a plurality of 2D images of the inspection site;

using a spatial learning module to generate a 3D spatial information of the inspection site according to the plurality of 2D images;

using a path generation module to generate an inspection path information based on the 3D spatial information, wherein the generation of the inspection path information comprises:

performing a plurality of manual operations to capture the plurality of 2D images;

using the spatial learning module to generate the 3D spatial information;

recording a plurality of manual inspection paths of the inspection device and the 3D spatial information corresponding to each of the plurality of manual inspection paths;

establishing an inspection path generation network of the path generation module based on the plurality of manual inspection paths and the 3D spatial information;

using the inspection path generation network to generate a virtual inspection path based on the 3D spatial information; and applying a discrimination network to compare the virtual inspection path with the manual inspection paths and providing a comparison feedback to the inspection path generation network based on a comparison result; and using a motion device to move the inspection device to the inspection site according to the inspection path information for performing the bio-specimens collection and/or inspection.

12. The non-transitory computer-readable recording medium according to claim 11, wherein the plurality of 2D images of the inspection site are captured by the image processing module from different viewing angles.

13. The non-transitory computer-readable recording medium according to claim 11, wherein the generation of the 3D spatial information comprises using a 3D learning network of the spatial learning module to generate the 3D spatial information comprising a plurality of depth information, and a plurality of color information expressed in a form of RGBD.

14. The non-transitory computer-readable recording medium according to claim 11, wherein the inspection path generation network of the path generation module is used to generate the inspection path information in an automatic inspection stage.

15. A non-transitory computer-readable recording medium, wherein the non-transitory computer-readable recording medium stores a program code, and the program code is executed by a processor to execute steps of:

commanding an inspection device to approach an inspection site of bio-specimens;

commanding an image processing module to capture and process a plurality of 2D images of the inspection site;

commanding a spatial learning module to generate a 3D spatial information of the inspection site according to the 2D images;

commanding a path generation module to generate an inspection path information based on the 3D spatial information, wherein the generation of the inspection path information comprises:

performing a plurality of manual operations to capture the plurality of 2D images;

using the spatial learning module to generate the 3D spatial information;

recording a plurality of manual inspection paths of the inspection device and the 3D spatial information corresponding to each of the plurality of manual inspection paths;

establishing an inspection path generation network of the path generation module based on the plurality of manual inspection paths and the 3D spatial information;

using the inspection path generation network to generate a virtual inspection path based on the 3D spatial information; and applying a discrimination network to compare the virtual inspection path with the manual inspection paths and providing a comparison feedback to the inspection path generation network based on a comparison result; and commanding a motion device to move the inspection device to the inspection site according to the inspection path information for performing an inspection operation.

* * * * *